US008262579B2

(12) United States Patent
Parlikar et al.

(10) Patent No.: US 8,262,579 B2
(45) Date of Patent: Sep. 11, 2012

(54) SYSTEM AND METHOD FOR PREDICTION AND DETECTION OF CIRCULATORY SHOCK

(75) Inventors: Tushar A. Parlikar, Cambridge, MA (US); Thomas Heldt, Cambridge, MA (US); George C. Verghese, Newton, MA (US); Roger G. Mark, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1055 days.

(21) Appl. No.: 12/122,247

(22) Filed: May 16, 2008

(65) Prior Publication Data

US 2008/0287753 A1    Nov. 20, 2008

Related U.S. Application Data

(60) Provisional application No. 60/938,253, filed on May 16, 2007, provisional application No. 60/938,257, filed on May 16, 2007.

(51) Int. Cl.
*A61B 5/02* (2006.01)
(52) U.S. Cl. ....................................................... 600/485
(58) Field of Classification Search .......................... None
See application file for complete search history.

(56) References Cited

U.S. PATENT DOCUMENTS

| | | | |
|---|---|---|---|
| 4,236,527 A | 12/1980 | Newbower et al. | |
| 4,507,974 A | 4/1985 | Yelderman | |
| 5,146,414 A | 9/1992 | McKown et al. | |
| 5,153,178 A | 10/1992 | Maroko | |
| 5,400,793 A | 3/1995 | Wesseling | |
| 5,687,733 A | 11/1997 | McKown | |
| 6,485,431 B1 | 11/2002 | Campbell | |
| 6,758,822 B2 | 7/2004 | Romano | |
| 2003/0040675 A1* | 2/2003 | Sharrock | 600/490 |
| 2004/0158163 A1 | 8/2004 | Cohen et al. | |
| 2004/0249297 A1 | 12/2004 | Pfeiffer et al. | |
| 2004/0254483 A1 | 12/2004 | Zdeblick et al. | |
| 2005/0015009 A1 | 1/2005 | Mourad et al. | |
| 2005/0096557 A1* | 5/2005 | Vosburgh et al. | 600/509 |
| 2005/0124903 A1 | 6/2005 | Roteliuk et al. | |
| 2005/0124904 A1 | 6/2005 | Roteliuk | |
| 2006/0008923 A1* | 1/2006 | Anderson et al. | 436/518 |
| 2006/0178589 A1 | 8/2006 | Dobak | |
| 2006/0235323 A1 | 10/2006 | Hatib et al. | |
| 2007/0016031 A1 | 1/2007 | Mourad et al. | |
| 2007/0024946 A1 | 2/2007 | Panasyuk et al. | |
| 2007/0197921 A1 | 8/2007 | Cohen et al. | |
| 2008/0015451 A1 | 1/2008 | Hatib et al. | |
| 2008/0287812 A1 | 11/2008 | Parlikar et al. | |
| 2008/0294057 A1 | 11/2008 | Parlikar et al. | |
| 2009/0112113 A1 | 4/2009 | Mukkamala | |

FOREIGN PATENT DOCUMENTS

| | | |
|---|---|---|
| WO | WO2007/109059 | 9/2007 |
| WO | WO-2008/144404 A1 | 11/2008 |
| WO | WO-2008/144490 A1 | 11/2008 |

OTHER PUBLICATIONS

International Search Report and Written Opinion for International Application PCT/US08/063915, Oct. 3, 2008.
Parlikar, T. et al., "Model-based estimation of cardiac output and total peripheral resistance," Computers in Cardiology, vol. 34 (2007) pp. 379-382.
Cheatham, Michael L. et al., "Shock: an overview," Orlando Regional Medical Center, 2004, available online at http://www.surgicalcriticalcare.net/Lectures/shock_overview.pdf.
International Preliminary Report on Patentability and Written Opinion for International Application No. PCT/US2008/063915 dated Nov. 26, 2009.
International Preliminary Report on Patentability and Written Opinion for International Application No. PCT/US2008/063872 dated Nov. 26, 2009.
International Search Report and Written Opinion of the International Searching Authority for International Application No. PCT/US08/63872 dated Sep. 26, 2008.
International Preliminary Report on Patentability and Written Opinion for International Application No. PCT/US2008/063725 dated Nov. 26, 2009.
International Search Report and Written Opinion of the International Searching Authority for International Application No. PCT/US08/63725 dated Sep. 26, 2008.
Parlikar et. al., "Cycle-Averaged Models of Cardiovascular Dynamics," IEEE Trans. on Circuits and Systems—1, vol. 53, No. 11, pp. 2459-2468, Nov. 2006.

* cited by examiner

*Primary Examiner* — Tracy Vivlemore
(74) *Attorney, Agent, or Firm* — Ropes & Gray LLP

(57) ABSTRACT

Systems and methods for prediction and detection of circulatory shock using estimates or measurements of arterial blood pressure, heart rate, stroke volume, cardiac output, total peripheral resistance, cardiac ejection fraction, cardiac contractility and ventricular end-diastolic volume are provided. These estimates and measurements are used to determine a type of circulatory shock. In some embodiments, the type of circulatory shock is determined to be one of septic shock, hypovolemic shock, anaphylactic shock, hemorrhagic shock, and cardiogenic shock.

41 Claims, 6 Drawing Sheets

FIG. 4

| Dog | EF (%) Range | LVEDV (ml) Range | LVESV (ml) Range | HR (bpm) Range | cABP (mmHg) Range |
|---|---|---|---|---|---|
| 1 | 53-90 | 28-46 | 3-20 | 94-181 | 50-160 |
| 2 | 30-86 | 17-30 | 3-21 | 88-179 | 56-99 |
| 3 | 55-76 | 19-28 | 6-11 | 142-197 | 57-120 |

SYSTEM AND METHOD FOR PREDICTION AND DETECTION OF CIRCULATORY SHOCK

CROSS REFERENCE TO RELATED APPLICATIONS

The instant application claims priority from provisional application No. 60/938,257 filed May 16, 2007, and provisional application No. 60/938,253, filed May 16, 2007, the contents of each of which are incorporated herein by reference in its entirety.

STATEMENT REGARDING FEDERALLY SPONSORED RESEARCH OR DEVELOPMENT

This invention was made in part with Government support under Contract No. R01 EB001659, awarded by the National Institute of Biomedical Imaging and Bioengineering, a part of the United States' National Institutes of Health. The Government has certain rights in this invention.

FIELD OF THE INVENTION

This invention relates to systems and methods for prediction and detection of circulatory shock using estimates or measurements of heart rate, arterial blood pressure, cardiac output, total peripheral resistance, cardiac ejection fraction, and ventricular end-diastolic volume.

BACKGROUND OF THE INVENTION

In modern intensive care units (ICUs), among other clinical settings, a vast and varied amount of physiological data is measured and collected, with the intent of providing clinicians with detailed information about the physiological state of each patient. The data include measurements from the bedside monitors of heavily instrumented patients, imaging studies, laboratory test results, and clinical observations. The clinician's task of integrating and interpreting the data, however, is complicated by the sheer volume of information and the challenges of organizing it appropriately. This task is made even more difficult by ICU patients' frequently-changing physiological state.

In these settings, several cardiovascular variables are used clinically to assess the performance of the heart as an effective pump. Chief among them are arterial blood pressure, cardiac output, total peripheral resistance, ventricular end-diastolic volume and pressure, contractility, and ejection fraction (all defined below).

Cardiac output (CO) is the amount of blood the heart pumps out over a unit of time. Typical values of CO in resting adults range from 3 liters/minute to 6 liters/minute. One basis for estimating or measuring CO is the formula:

$$CO = HR \times SV \quad (EQ. 1)$$

where SV is cardiac stroke volume and HR is heart rate. If SV is measured in liters/beat and HR is measured in beats per minute, then CO is given in liters/minute, although any other units of volume and time may be used. Another basis for estimating or measuring CO is:

$$CO = MAP/TPR \quad (EQ. 2)$$

where MAP is mean arterial blood pressure (Arterial blood pressure is ABP) and TPR is total peripheral resistance.

End-diastolic volume (EDV) is the volume in the ventricle at the end of the ventricular filling phase of the cardiac cycle. End-systolic volume (ESV) is the volume in the ventricle at the end of the ejection phase of the cardiac cycle.

Stroke volume (SV) of the heart or of the left or right ventricle may be defined as the difference between end-systolic volume and end-diastolic volume, namely:

$$SV = EDV - ESV \quad (EQ. 3)$$

Ejection fraction (EF) is defined as the ratio of the stroke volume (SV) to the ventricular end-diastolic volume (EDV) and is expressed in percent, namely:

$$EF = SV/EDV = (EDV - ESV)/EDV \quad (EQ. 4)$$

More simply, EF represents the percentage of the end-diastolic volume in a ventricular chamber that is ejected per beat. EF can be measured in the right ventricle (RV) or the left ventricle (LV). Thus, RVEF is right ventricular ejection fraction and LVEF is left ventricular ejection fraction.

In this application, embodiments are presented with respect to the left ventricle, for which Applicants sometimes write EF instead of LVEF. The methods and systems described herein can easily be extended to the right ventricle.

Cardiac contractility is a measure of ventricular elastance at the end of the ejection. Contractility is usually thought of as being a measure of ventricular elastance for the left ventricle, i.e., cardiac contractility and left-ventricular contractility are equivalent terms in the art.

Chronically elevated end-diastolic pressures and volumes indicate poor pump performance, as do low states of contractility and a reduced ejection fraction [1]. (Numbers in square brackets refer to the reference list included herein. The contents of all these references are incorporated herein by reference.) Cardiac output and Total Peripheral Resistance can also be indicators of poor cardiovascular system performance. Ideally, these variables should be measured non- to minimally invasively for establishing initial diagnoses and tracked continuously for monitoring of disease progression and titration of therapeutic interventions.

The current clinical gold-standard measurements for measuring these variables, however, are costly, require expert operators, and are only performed intermittently. For instance, cardiac blood volumes are commonly measured echocardiographically: a skilled operator performs intermittent ultrasonic evaluations of the heart during which the relevant cardiac volumes are determined. Cardiac ejection fraction is then calculated from the resultant end-systolic and end-diastolic volumes.

Of particular relevance in clinical settings (e.g., in the ICU or the emergency room, ER) is the problem of distinguishing between three types of circulatory shock [which can be thought of as severe hypotension—or dangerously low mean arterial blood pressure or MAP], which may include, among others, septic shock (due to infections in the systemic vasculature), cardiogenic shock (relating to heart (pump) failure associated with myocardial infarction, cardiomyopathy, cardiac tamponade, etc.), hypovolemic shock (relating to low blood volume, e.g., as a consequence of bleeding or hemorrhage), anaphylactic shock (relating to circulatory shock due to a severe allergic reaction).

In ICUs or ERs, clinical interventions for each of these types of circulatory shock are different. In the case of hypovolemic shock, for example, one would try to increase a patient's blood volume, perhaps with a saline infusion or other appropriately-chosen fluid replacement therapy. With cardiogenic shock, on the other hand, one would try to reduce the load on the heart (either the inlet (preload) or outlet (afterload) pressures acting on the patient's heart), perhaps by administering drugs that would reduce the patient's vascular resistance or increase cardiac contractility. For patients with sepsis, intravenous fluid administration and/or medications that increase MAP by increasing TPR may be given.

The therapeutic interventions given to patients for circulatory shock or low MAP can often be incorrect if the relevant clinical information is not available. For instance, for patients with CHF, one would attempt diuresis (say, by giving a diuretic drug such as furosemide ('Lasix') to reduce the preload on the heart and remove any water that may have accumulated in the lungs (a condition known as pulmonary edema). On the other hand, for patients with hypovolemia, one would give the patient a bolus of fluid, e.g., saline infusion, in an attempt to increase distending blood volume, and in turn, MAP. If one were to give a patient with CHF a fluid bolus, this would worsen the preload on the heart and probably worsen the patient's pulmonary edema symptoms [3].

Currently, it is quite difficult to determine the root cause of a patient's shock, mainly for two reasons. First, CO, EF, and LVEDV are not frequently measured in the ICU. Of these, CO can be measured with relative ease once a pulmonary artery catheter is in place, but this is an invasive procedure that is reserved for the sickest of patients [3]. Second, for many ICU patients, there is always the possibility that the shock is a result of multiple organs failing, i.e., they may be suffering from heart failure and a systemic infection.

Thus, methods and apparatus for effectively establishing initial differential diagnoses for circulatory shock, and for continuous monitoring of the disease progression are needed. Such methods would greatly facilitate the monitoring, diagnosis, and treatment of cardiovascular disease.

The statements in this section merely provide background information related to the present disclosure and may not constitute prior art

SUMMARY OF THE INVENTION

One of the objectives of the present invention is to provide systems and methods for predicting and detecting circulatory shock using estimates and/or measurements of arterial blood pressure, heart rate, cardiac output, total peripheral resistance, cardiac ejection fraction, and ventricular end-diastolic volume. The embodiments described below will use, for illustrative purposes only, a central or peripheral arterial blood pressure and involve monitoring of left-ventricular performance. However, those skilled in the art will recognize that these examples would translate directly to the monitoring of right-ventricular performance by analyzing the pulmonary artery pressure waveform.

In one aspect, the invention relates to a system for predicting or detecting circulatory shock comprising a blood pressure measuring device, a processor, a display, a user interface, and a memory storing computer executable instructions, which when executed by the processor cause the processor to receive measurements of arterial blood pressure from the blood pressure device, compute mean arterial blood pressure from the received arterial blood pressure measurements, receive or compute estimates of at least one of heart rate, total peripheral resistance, cardiac output, stroke volume, ejection fraction, ventricular end-diastolic volume, and cardiac contractility, and classify each of these estimates as one of low, normal, or high, and predict or detect a type of circulatory shock based in part on one or more values of the received measurements and estimates. The received or computed estimates may also be estimates that are proportional or uncalibrated estimates.

In preferred embodiments, the type of shock includes one of septic shock, hypovolemic shock, anaphylactic shock, hemorrhagic shock, and cardiogenic shock. In one embodiment, the type of circulatory shock is determined to be (a) septic shock if the mean arterial blood pressure is low, total peripheral resistance is low, heart rate is high, ejection fraction is normal or high, cardiac output is low or high; (b) hypovolemic shock if the mean arterial blood pressure is low, total peripheral resistance is high, heart rate is high, ejection fraction is normal or high, end-diastolic volume is low, cardiac output is low or high; (c) anaphylactic shock if the mean arterial blood pressure is low, total peripheral resistance is low, heart rate is high, ejection fraction is normal or high, cardiac output is high; (d) hemorrhagic shock if the mean arterial blood pressure is low, total peripheral resistance is high, heart rate is high, ejection fraction is normal or high, end-diastolic volume is low, cardiac output is low or high; and (e) cardiogenic shock if the mean arterial blood pressure is low, total peripheral resistance is high, ejection fraction is low, end-diastolic volume is high, cardiac output is low. In some embodiments, this determination is carried out using a lookup table. In other embodiments, this determination is carried out using a machine learning algorithm. In some embodiments, the machine learning algorithm includes a Bayesian network. In other embodiments, the machine learning algorithm includes a neural network. In other embodiments, the machine learning algorithm includes a fuzzy logic model. In some embodiments, the determination involves using population-specific data. In other embodiments, the determination involves using patient-specific data.

In one embodiment, the system also includes an electrocardiogram device. In an embodiment, the blood pressure measuring device is a noninvasive blood pressure device. In some embodiments, this noninvasive blood pressure device is a photoplethysmographic blood pressure measuring device. In other embodiments, this noninvasive blood pressure device is a tonometric blood pressure measuring device.

In an embodiment, the arterial blood pressure is measured at a central artery of the cardiovascular system. In another embodiment, the arterial blood pressure is measured at a peripheral artery of the cardiovascular system. In an embodiment, the arterial blood pressure is measured at a pulmonary artery of the cardiovascular system.

In one embodiment, the processor additionally classifies the received measurements and the received or computed estimates as one of low, normal or high. The processor then determines the type of shock as being one of septic shock, hypovolemic shock, anaphylactic shock, hemorrhagic shock, and cardiogenic shock based in part on this classification.

In another embodiment, the processor displays the received measurements of arterial blood pressure, and the received or computed estimates of heart rate, total peripheral resistance, cardiac output, ejection fraction, cardiac contractility, and ventricular end-diastolic volume. In another embodiment, the processor displays the type of circulatory shock.

According to another aspect, the invention relates to a method for predicting or detecting circulatory shock, the method comprising receiving measurements of arterial blood pressure, computing mean arterial blood pressure from the received arterial blood pressure measurements, receiving or computing estimates of at least one of heart rate, total peripheral resistance, cardiac output, ejection fraction, cardiac contractility, and ventricular end-diastolic volume, and predicting or detecting a type of circulatory shock based in part on one or more of the received measurements and the received or computed estimates.

BRIEF DESCRIPTION OF THE DRAWINGS

The invention may be better understood from the following illustrative description with reference to the following drawings.

FIG. 4 is a table of population statistics for the canine animal experiment data set. The data was obtained from Professor Ramakrishna Mukkamala at Michigan State University and was also used in [3];

DESCRIPTION OF CERTAIN ILLUSTRATIVE EMBODIMENTS

To provide an overall understanding of the invention, certain illustrative embodiments will now be described. However, it will be understood by one of ordinary skill in the art that the methods described herein may be adapted and modified as is appropriate for the application being addressed and that the systems and methods described herein may be employed in other suitable applications, and that such other additions and modifications will not depart from the scope hereof.

Figure 1:
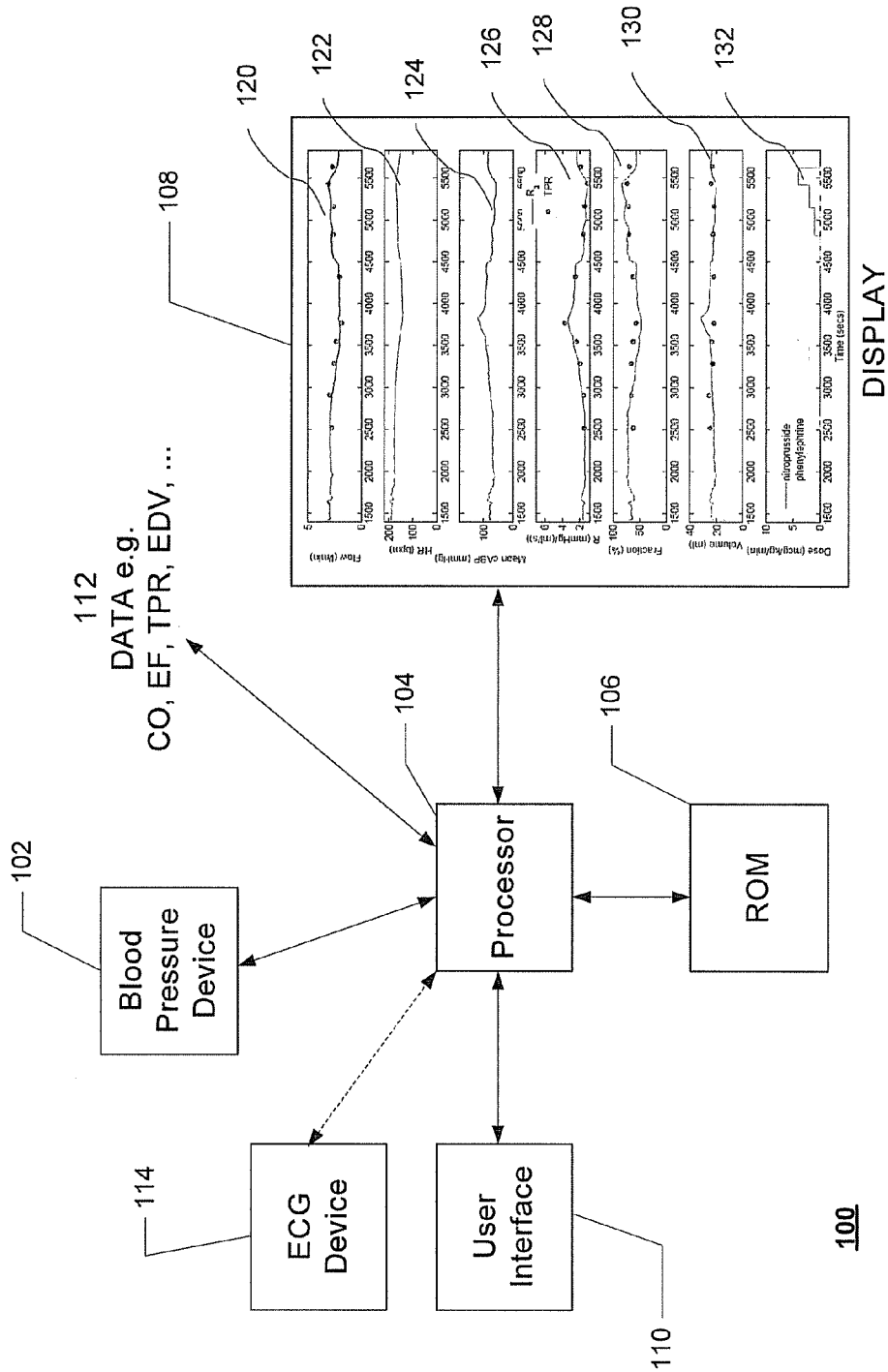
FIG. 1 is a block diagram of a system for shock prediction and detection, according to an illustrative embodiment of the invention.

FIG. 1 is a block diagram of a shock prediction and detection system 100 in which the present invention's teachings may be implemented. Such a system may be deployed in an intensive care unit, or other clinical setting. In such clinical settings, Applicants envision providing beat-to-beat estimates of CO, HR, SV, TPR, EF, Contractility, and EDV to clinicians and nurses, together with a classification of the type of circulatory shock, allowing them to quickly decide on therapeutic interventions for ICU patients. Such patients may have symptoms of one or more of hypovolemic shock, hemorrhagic shock, anaphylactic shock, septic shock, or cardiogenic shock, among other types of circulatory shock.

System 100 in FIG. 1 includes blood pressure measuring device 102 which provides measurements of arterial blood pressure, data 112, processor 104, memory 106 e.g. Read-Only Memory (ROM), display 108, user interface 110. Optionally, the system may include an electrocardiogram (ECG) device 114 from which electrocardiographic measurements are received. The processor 104 operates on blood pressure data from blood pressure measuring device 102 and data 112 in accordance with computer-executable instructions loaded into memory 106. The instructions will ordinarily have been loaded into the memory from local persistent storage in the form of, say, a disc drive with which the memory communicates. The instructions may additionally or instead be received by way of user interface 110. The system may also receive user input from devices such as a keyboard, mouse, or touch-screen. These inputs are used to configure the display, as well as provide instructions to the processor. Blood pressure measuring device 102 may be an invasive or a noninvasive device. Blood pressure measuring device 102 may be a photoplethysmographic or a tonometric device. Blood pressure measuring device 102 may also be a catheter-based blood pressure measuring system. The blood pressure may be measured at a central, a pulmonary, or a peripheral artery in the cardiovascular system.

Data 112 which is received by processor 104 of system 100 may include estimates of stroke volume, cardiac output, heart rate, arterial blood pressure, total peripheral resistance, cardiac contractility, ejection fraction, and ventricular end-diastolic volume. The received or computed estimates may be also be estimates that are proportional or uncalibrated estimates, e.g., $\beta*ECO$, where $\beta$ is a multiplicative calibration parameter for estimated cardiac output (ECO).

The stroke volume or cardiac output estimates may also be obtained from arterial blood pressure measurements by processor 104 of system 100 of FIG. 1, for instance, using methods described in [3, 4], or commonly-owned, co-pending U.S. patent application Ser. No. 12/121,042 to Parlikar et al., the contents of which are incorporated herein in their entirety, or other CO or SV estimation systems. Examples include systems directed to estimating CO (and hence SV) via thermodilution e.g. U.S. Pat. No. 4,236,527 to Newbower et al., U.S. Pat. No. 4,507,974 to Yelderman, U.S. Pat. No. 5,146,414 to McKown et al., and U.S. Pat. No. 5,687,733 to McKown et al., the contents of each of which are incorporated herein in their entirety, or systems directed to estimating CO (and hence SV) from arterial blood pressure measurements, e.g., U.S. Pat. No. 5,400,793 to Wesseling, U.S. Patent Application Publication No. 20040158163 to Cohen et al., U.S. Patent Application Publication No. 20050124903 to Roteliuk et al., U.S. Patent Application Publication No. 20050124904 to Roteliuk, U.S. Patent Application Publication No. 20060235323 to Hatib et al., U.S. Patent Application Publication No. 20080015451 to Hatib et al., the contents of each of which are incorporated herein in their entirety.

Heart rate may be obtained from either computations involving measurements received from ECG device 114 or blood pressure measuring device 102, or it may be received as part of data 112.

Estimates of ejection fraction, end-diastolic volume, and cardiac contractility may also be received as part of data 112. Estimates of these three variables may also be obtained from arterial blood pressure measurements operated on by processor 104 of system 100 of FIG. 1, for instance, using methods described in [3], or commonly-owned, co-pending U.S. patent application Ser. No. 12/121,878 to Parlikar et al., the contents of which are incorporated herein in their entirety, or other EF estimation systems, e.g., WIPO patent application publication No. WO2007109059 to Mukkamala, the contents of which are incorporated herein in their entirety.

Processor 104 of system 100 of FIG. 1 may operate on Data 112 and measurements received from blood pressure measuring device 102 and/or ECG device 114 to classify the received or computed estimates and received measurements as being indicative of a type of circulatory shock. This type of circulatory shock may include septic shock, hemorrhagic shock, hypovolemic shock, cardiogenic shock, or anaphylactic shock, as will be described in reference to FIG. 2.

Processor 104 of system 100 of FIG. 1 may display the received or computed estimates of, among others, arterial blood pressure or mean arterial blood pressure 124, heart rate 122, stroke volume, total peripheral resistance 126, cardiac output 120, cardiac contractility, ejection fraction 128, and end-diastolic volume 130, and other information e.g. drug infusions 132 for an animal or patient, type of circulatory shock that is predicted or detected or determined, on display 108. A user may interact with the display via user interface 110 to select which of these variables to display, and may manipulate the display to change the scales on the temporal or other display axes.

Figure 2:
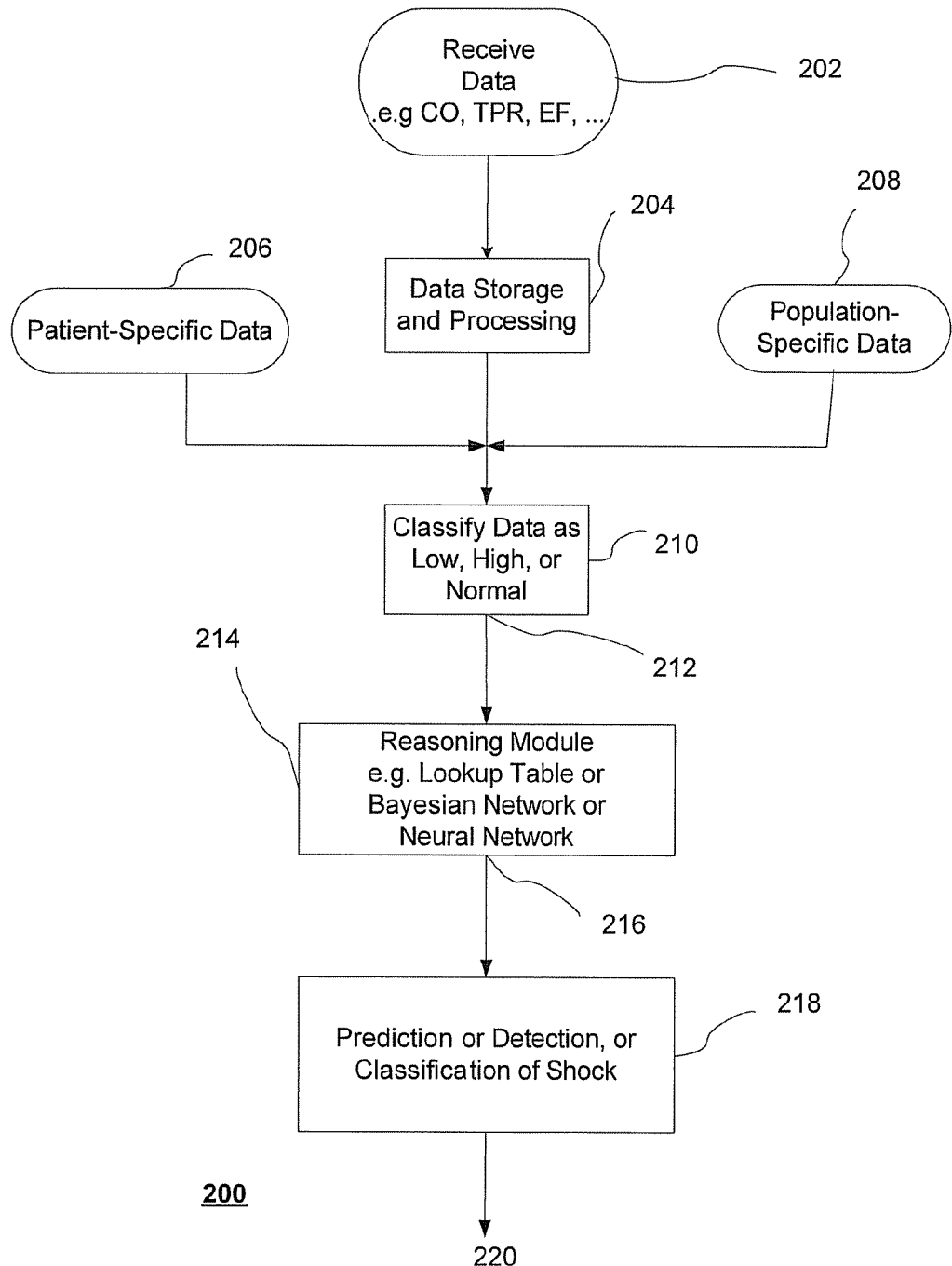
FIG. 2 is a process flow diagram suitable for predicting or detecting shock with the system of FIG. 1, according to an illustrative embodiment of the invention.

FIG. 2 is an exemplary process flow diagram 200 for determining, predicting, or detecting a type of circulatory shock, which may be initiated by processor 104 of system 100 of FIG. 1. The process flow diagram 200 includes the steps 202, 204, 206, 208, 210, 214, and 218, with outputs (or intermediate outputs) 212, 216, and 220. The determination, prediction, or detection of the type of circulatory shock is based in part on received measurements of ECG or ABP, and on received or computed measurements of one or more of heart rate, total peripheral resistance, cardiac output, cardiac contractility, stroke volume ejection fraction, and end-diastolic volume.

In one embodiment, at step 202 of process 200 of FIG. 2, data (e.g. ECG measurements, ABP measurements, and estimates of one or more of SV, CO, HR, TPR, Contractility, EDV and EF) are received. This data could be thought of as data 112 that is received by processor 104 of system 100 in FIG. 1. In alternative embodiments, estimates of one or more of SV, CO, HR, TPR, Contractility, EDV and EF are computed from the arterial blood pressure measurements, and possibly true or reference (calibration) measurements of these estimates. These computations could be carried out using methods described in [3], or commonly-owned, co-pending U.S. patent application Ser. No. 12/121,878 to Parlikar et al. or other EF estimation systems, e.g., WIPO patent application publication No. WO2007109059 to Mukkamala.

At step 204 of process 200 of FIG. 2, the received measurements of ABP and/or ECG, and the received or computed estimates of SV, CO, HR, TPR, contractility, EDV and EF are stored. Other data processing steps, e.g., buffering, re-sampling, or windowing, may be performed during this step.

In some embodiments, at step 206 of process 200 of FIG. 2, patient-specific data, which may include, among others, a patient's medical information such as, for example, blood chemistry results, imaging study results, past medical history, temporal trends in ECG, ABP, SV, CO, HR, TPR, contractility, EDV or EF, etc. In other embodiments, at step 208, population-specific data, which may include, among others, a patient population's medical information, e.g., average, maximum or minimum ejection fraction measured for patients with acute myocardial infarction, average, maximum, or minimum creatinine levels for patients with septic shock or sepsis, etc. In some embodiments, the patient-specific and population-specific data may be received at step 202 of process 200 of FIG. 2 along with the other measurements and estimates.

In some embodiments, at step 210 of process 200 in FIG. 2, the processed data (which include, among others, received measurements, received or computed estimates, received patient-specific data, received population-specific data) may be classified into low, normal, or high values. In alternative embodiments, such a classification of the processed data may not be carried out, and the process 200 would not include step 210.

In preferred embodiments, at step 214 of process 200 of FIG. 2, a reasoning module is used to predict, detect, determine, or classify the type of circulatory shock in step 218. Such a reasoning module could reside within processor 104 of system 100 of FIG. 1. In preferred embodiments, the type of circulatory shock is classified into one or more of anaphylactic shock, septic shock, cardiogenic shock, hypovolemic shock, or hemorrhagic shock.

In preferred embodiments, the reasoning module of step 214 of process 200 of FIG. 2 does the prediction, detection, determination, or classification of type of circulatory shock based on the processed data which include, among others, received measurements, received or computed estimates, received patient-specific data, received population-specific data. For instance, CO and LVEDV (or left-ventricular end-diastolic pressure, LVEDP) by themselves may be used to determine whether a patient has cardiogenic shock due to left-ventricular failure, or hypovolemic or hemorrhagic shock due to bleed. In particular, if reasoning module receives estimates that indicate low CO and high LVEDV, the reasoning module of step 214 may indicate left-ventricular failure and cardiogenic shock. If, on the other hand, the reasoning module of step 214 receives estimates that indicate low CO and low LVEDV, it may indicate hypovolemic or hemorrhagic shock, which would be indicative of hypovolemia. The reasoning module of step 214 could use ejection fraction to allow for the additional distinction between sepsis (and, by inference, septic shock), cardiac failure (and, by inference, cardiogenic shock) and hypovolemia (and, by inference, hypovolemic or hemorrhagic shock), since sepsis and hypovolemia are usually not associated with low EF. In alternative embodiments, the determination, prediction, detection or classification of the type of circulatory shock could also be achieved using a lookup table or a machine learning algorithm. For instance, one could use a machine learning algorithm involving a Bayesian network or a neural network or a fuzzy logic model in the reasoning module of step 214 of process 200 of FIG. 2.

Figure 3:
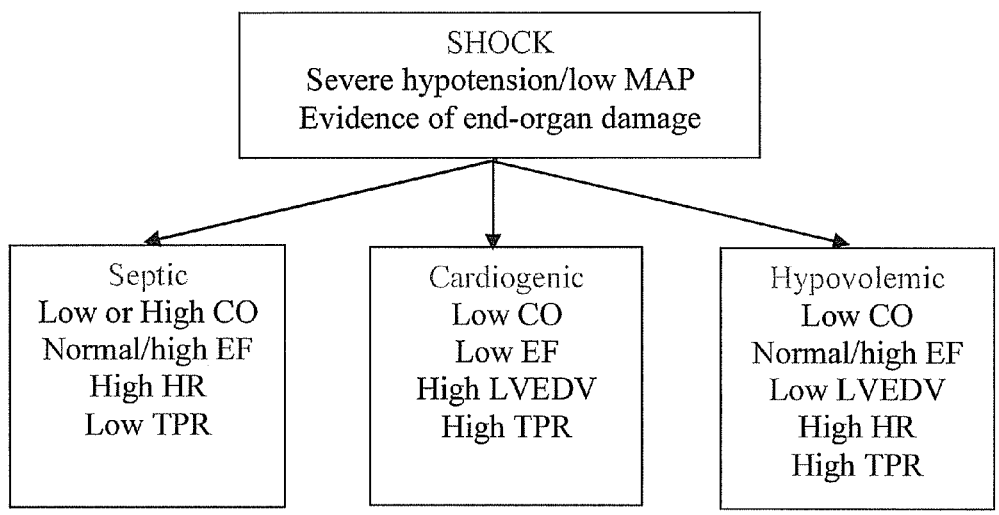
FIG. 3 is an example of a differential diagnosis for circulatory shock with a lookup table, according to an illustrative embodiment of the invention.

FIG. 3 shows an exemplary classification of type of circulatory shock, according to an illustrative embodiment of the invention. Such a classification could be performed by system 100 of FIG. 1 using the steps outlined with reference to process 200 of FIG. 2. In FIG. 3, the received measurements and/or estimates of ABP, HR, TPR, CO, EF, and LVEDV are processed and classified into low, normal, or high values. This classification may be performed using patient- or population-specific data. Depending on the classification of the received measurements and/or estimates in the exemplary classification of FIG. 3, the classified measurements and data are used to differentiate between septic, cardiogenic, and hypovolemic shock. For instance, if CO is low or high, EF is normal or high, HR is high, and TPR is high, system 100 of FIG. 1 would determine the type of (circulatory) shock as septic. If, on the other hand, CO is low, EF is low, LVEDV is high, and TPR is high, system 100 of FIG. 1 would determine the type of (circulatory) shock to be cardiogenic. Finally, if CO is low, EF is normal or high, LVEDV is low, HR is high, and TPR is high, then system 100 of FIG. 1 would determine the type of (circulatory) shock to be hypovolemic.

In this manner, a classification of the type of circulatory shock can be robustly obtained. As will be described below in reference to FIGS. 4-6, the results obtained using estimation system 100 of FIG. 1, are accurate enough for clinical application. In the discussion below, Applicants will give a detailed description of experimental results using an animal (canine or Animal) data set, with reference to FIGS. 4-6.

Animal (Canine) Data Set

The animal (canine) experiment data set was the result of a study on three beagles (weighing 10-15 kg) approved by the Michigan State University All-University Committee on Animal Use and Care. Applicants graciously acknowledge Professor Ramakrishna Mukkamala's willingness to make his data set available for the experiments described herein.

Dog 1 was intubated under anesthesia and mechanically ventilated. Once intubated, the Animal underwent a thoracotomy and an aortic flow transducer was placed. This Animal was allowed ten days to recover from this major surgery.

The same experimental protocol was then performed on each of the three dogs—one with the chronic instrumentation described above, and two others. Each animal was anesthetized, but not mechanically ventilated. Catheters were placed in the thoracic aorta to measure cABP, and in the femoral artery to measure fABP. A syringe pump catheter was placed into a cephalic vein for drug administration, and ECG leads were placed on the animal. In each animal, over the course of approximately 1 hour, CO, EF, ABP, and HR were varied by one or more of the following interventions: volume infusions, fast hemorrhage, intravenous (IV) drugs (one or more of phenylephrine, nitroprusside, or dobutamine). During the experiment, 2-dimensional echocardiography measurements were intermittently used so as to obtain reference LVEDV, LVESV, and thus, EF measurements, according to the methods of Parlikar et al., as described in [3], or commonly-owned, co-pending U.S. patent application Ser. No. 12/121,878.

The table in FIG. 4 summarizes the population statistics for the canine data set. It is important to note that for dog 3, the variability in HR and mean cABP is particularly small. In fact, the beat-to-beat variability as measured by the beat-to-beat variability index (B2BVI)

$$B2BVI_b = \frac{1}{360} \sum_{n=b}^{b+360} \left(100 \frac{\Delta P_n}{PP_n}\right).$$ (EQ. 43)

where $PP_n$ is pulse pressure in the $n^{th}$ cardiac cycle, and $\Delta P_n$ is given by $$\Delta P_n = P(t_{n+1}) - P(t_n)$$ (EQ. 44)

and is the beat-to-beat pressure change at the beat or cycle onset times $t_n$ and $t_{n+1}$, does not exceed 1% for the entire record for Animal 3, does not exceed 3% for the entire record for Animal 2, and only exceeds 5% for a few windows of data for Animal 1, with most variability seen with the fABP waveform.

For Animal 1, the data set is comprised of measurements of central arterial blood pressure (cABP) measured at the aorta, carotid arterial blood pressure (carABP), and femoral arterial blood pressure (fABP), all sampled at 250 Hz with 16 bit resolution. In addition, there are intermittent echocardiography measurements of heart rate, left ventricular end-systolic volume and left ventricular end-diastolic volume, from which one can compute left ventricular ejection fraction using the EF and LVEDV methods of Parlikar et al. described in co-pending, commonly-owned U.S. patent application Ser. No. 12/121,878, the contents of which are incorporated herein in their entirety.

For dogs 2 and 3, the data set comprised of measurements of central arterial blood pressure (cABP) measured at the aorta sampled at 250 Hz with 16 bit resolution. Similar to Animal 1, there are intermittent echocardiography measurements of heart rate, left ventricular end-systolic volume (LVESV) and left ventricular end-diastolic volume (LVEDV), from which one can compute left ventricular ejection fraction (EF) using the EF and LVEDV methods of Parlikar et al. described in co-pending, commonly-owned U.S. patent application Ser. No. 12/121,878, the contents of which are incorporated herein in their entirety.

Using standard open-source algorithms on the cABP waveforms, we derived onset times for each cardiac beat and HR. We calculated systolic and diastolic cABP, and mean cABP for all three dogs. For Animal 1, we also calculated systolic and diastolic carABP, systolic and diastolic fABP, mean carABP, and mean fABP. We computed EF using the intermittent echocardiography measurements. For Animal 3 we averaged every three EF (or LVEDV) measurements as each consecutive set of three measurements was taken at about the same time instant. All the data processing and EF and LVEDV estimation algorithms were implemented in MATLAB™ R14 (Mathworks Inc., Natick, Mass.).

Experimental Results

We first used the available ABP waveforms in the canine data set to estimate beat-to-beat stroke volume using the CO estimation method of Parlikar et al. described in co-pending, commonly-owned U.S. patent application Ser. No. 12/121,042, the contents of which are incorporated herein in their entirety, and then used the estimated SV to obtain EF and EDV using the EF and EDV methods of Parlikar et al. described in co-pending, commonly-owned U.S. patent application Ser. No. 12/121,878, the contents of which are incorporated herein in their entirety.

Figure 5:
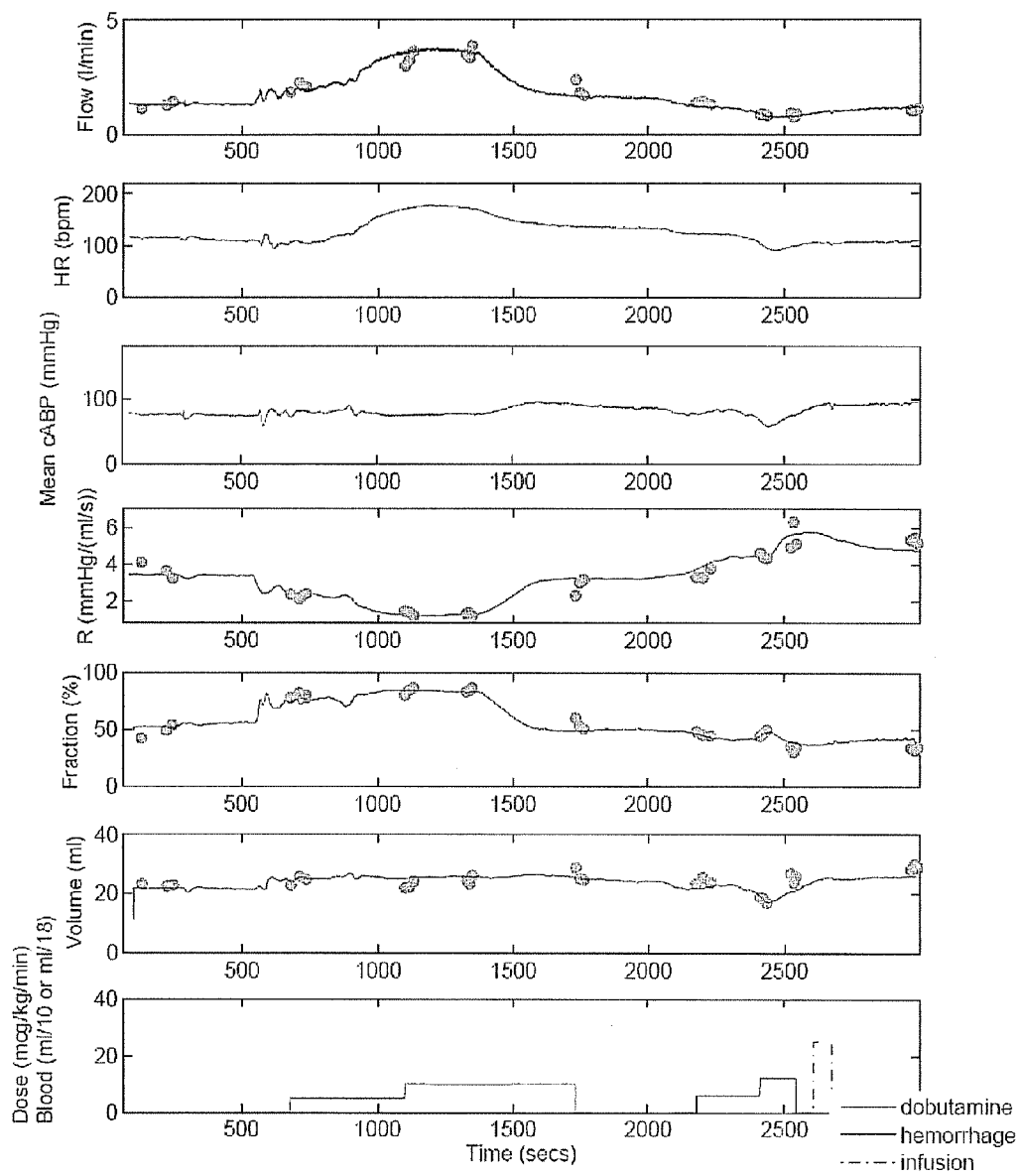
FIG. 5 is a graph of experimental results showing true and estimated CO (using cABP), HR, mean cABP, true and estimated TPR (using cABP), true and estimated EF (using cABP), true and estimated LVEDV (using cABP), and IV drugs for Animal 1 [3]

We plotted time series of estimated CO, TPR, EF, and LVEDV for dogs 1 and 2 in FIGS. 4 and 5, respectively.

In FIG. 5, when dobutamine is infused, we see a rapid increase in EF and a rapid decrease in both true and estimated TPR, while LVEDV stays approximately constant. Later in the record, when phenylephrine is infused, TPR increases, and as a result LVEDV increases. While these animal experiments were not designed as shock experiments per se, they do demonstrate that the estimated variables can be used to track the animal's response to pharmacological interventions/therapy.

Figure 6:
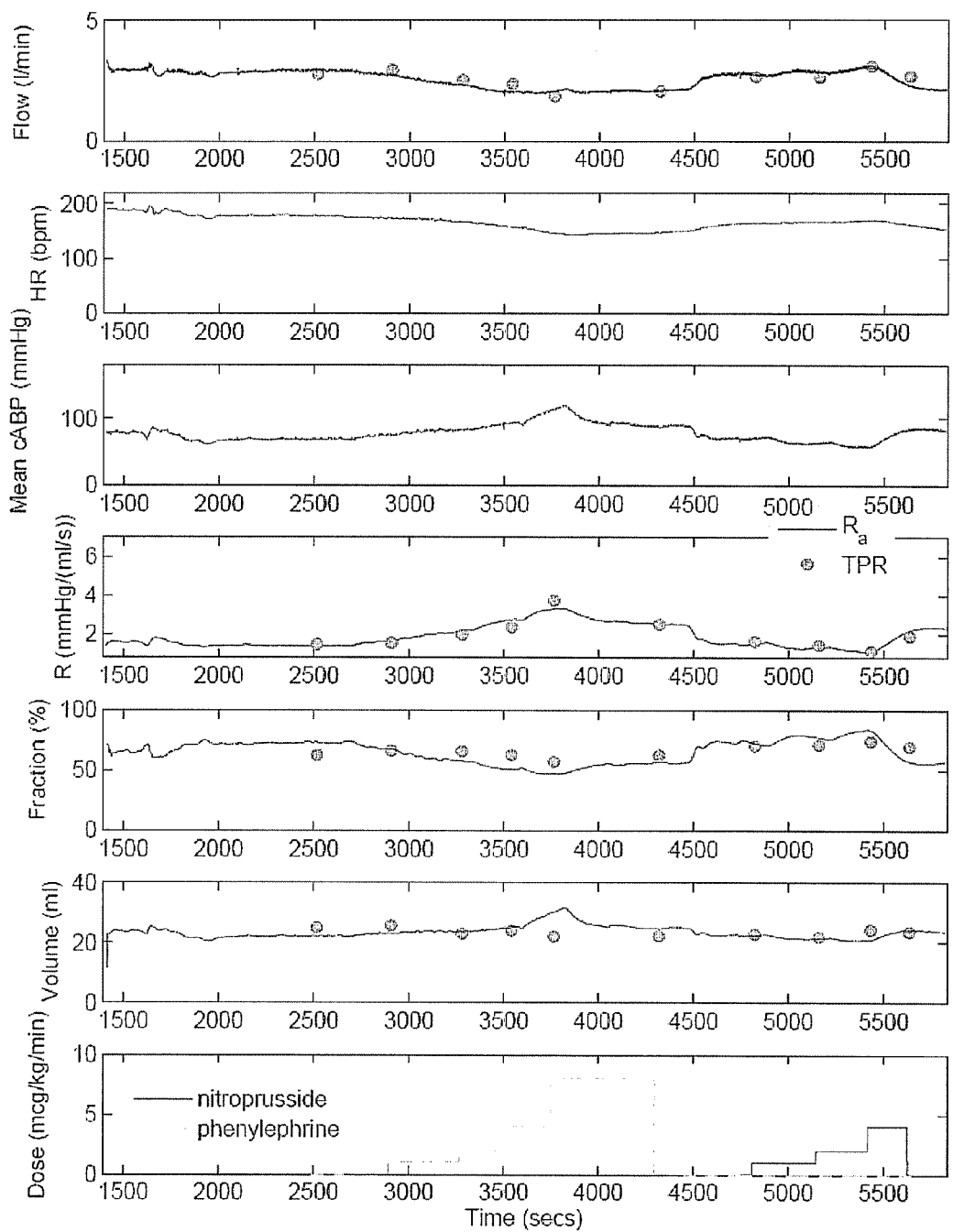
FIG. 6 is a graph of experimental results showing true and estimated CO (using cABP), HR, mean cABP, true and estimated TPR (using cABP), true and estimated EF (using cABP), true and estimated LVEDV (using cABP), and IV drugs for Animal 2 [3].

In FIG. 6, when dobutamine is infused, we see a rapid increase in EF and a rapid decrease in TPR, while LVEDV stays approximately constant. Later in the record, during the progressive hemorrhage, TPR and LVEDV increase very rapidly. During the volume infusion, TPR and LVEDV gradually increase. During the hemorrhage and volume infusion portions of data, EF stays approximately constant. This example demonstrates that tracking estimated or measured variables can give provide insight into the etiology of shock and the body's response and responsiveness to pharmacological intervention.

This invention may be embodied in other specific forms without departing from the spirit or essential characteristics thereof. The forgoing embodiments are therefore to be considered in all respects illustrative, rather than limiting of the invention.

List of References:

[1] V.-K. Lau and K. Sagawa. Model analysis of the contribution of atrial contraction to ventricular filling. Annals of Biomedical Engineering, 7:17-201, 1979.

[2] P. Marino. The ICU Book, chapter 9, pages 163-179. Lippincott Williams & Wilkins, Philadelphia, Pa., 3rd edition, 2007.

[3] T. Parlikar. Modeling and Monitoring of Cardiovascular Dynamics for Patients in Critical Care. Doctoral dissertation, Department of Electrical Engineering and Computer Science, Massachusetts Institute of Technology, Cambridge, Mass., June 2007.

[4] T. Parlikar, T. Heldt, G. Ranade, and G. Verghese. Model-based estimation of cardiac output and total peripheral resistance. Computers in Cardiology, 34:379-382, 2007.

[5] G. D. Rubenfeld, E. McNamara-Aslin, and L. Rubinson. The Pulmonary Artery Catheter, 1967-2007: Rest in Peace? JAMA, 298(4):458-461, 2007.

[6] M. Shah, L. Stevenson, C. Binanay, C. O'Conner, G. Sopko, and R. Califf. Impact of the pulmonary artery catheter in critically ill patients Journal of the American Medical Association, 294:1664-1670, 2005.

What is claimed is:

1. A system for predicting or detecting circulatory shock, comprising:
   a blood pressure measuring device;
   a processor;
   a display;
   a user interface; and
   a memory storing computer-executable instructions, which when executed by the processor cause the processor to:
      receive measurements of arterial blood pressure from the blood pressure measuring device;
      compute mean arterial blood pressure from the received arterial blood pressure measurements;
      compute estimates, based on the received arterial blood pressure measurements, of heart rate, total peripheral resistance, cardiac output, ejection fraction, and ventricular end-diastolic volume; and
      select a type of circulatory shock, from a plurality of types of circulatory shock, based on the computed mean arterial blood pressure and the computed estimates.

2. The system of claim 1, further comprising an electrocardiogram device, wherein selecting a type of circulatory shock is also based on measurements from the electrocardiogram device.

3. The system of claim 1, wherein the computer-executable instructions, when executed by the processor, cause the processor to display at least one of the received measurements and the computed estimates.

4. The system of claim 1, wherein the computer-executable instructions, when executed by the processor, cause the processor to display the selected type of circulatory shock.

5. The system of claim 1, wherein the type of circulatory shock is determined to be one of septic shock, hypovolemic shock, anaphylactic shock, and cardiogenic shock.

6. The system of claim 1, wherein the computed mean arterial blood pressure and the computed estimates are each classified as one of low, normal and high.

7. The system of claim 6, wherein the type of circulatory shock is determined to be one of septic shock, hypovolemic shock, anaphylactic shock, and cardiogenic shock.

8. The system of claim 7, wherein the type of circulatory shock is determined to be one or more of:
   (A) septic shock if the mean arterial blood pressure is low, total peripheral resistance is low, heart rate is high, ejection fraction is normal or high, and cardiac output is low or high;
   (B) hypovolemic shock if the mean arterial blood pressure is low, total peripheral resistance is high, heart rate is high, ejection fraction is normal or high, end-diastolic volume is low, and cardiac output is low or high;
   (C) anaphylactic shock if the mean arterial blood pressure is low, total peripheral resistance is low, heart rate is high, ejection fraction is normal or high, and cardiac output is high; and
   (D) cardiogenic shock if the mean arterial blood pressure is low, total peripheral resistance is high, ejection fraction is low, end-diastolic volume is high, and cardiac output is low.

9. The system of claim 1, 5, 7, or 8, wherein the selecting is done using a lookup table.

10. The system of claim 1, 5, 7, or 8, wherein the selecting is done using population-specific data.

11. The system of claim 1, 5, 7, or 8, wherein the selecting is done using patient-specific data.

12. The system of claim 1, 5, 7, or 8, wherein the selecting is done using a machine learning algorithm.

13. The system of claim 12, wherein the machine learning algorithm includes a Bayesian network.

14. The system of claim 12, wherein the machine learning algorithm includes a neural network.

15. The system of claim 12, wherein the machine learning algorithm includes a fuzzy logic model.

16. The system of claim 1, wherein the blood pressure measuring device is a noninvasive blood pressure measuring device.

17. The system of claim 16, wherein the noninvasive blood pressure measuring device is a photoplethysmographic blood pressure measuring device.

18. The system of claim 16, wherein the noninvasive blood pressure measuring device is a tonometric blood pressure measuring device.

19. The system of claim 1, wherein the arterial blood pressure is measured at a central artery of the cardiovascular system.

20. The system of claim 1, wherein the arterial blood pressure is measured at a peripheral artery of the cardiovascular system.

21. The system of claim 1, wherein the arterial blood pressure is measured at a pulmonary artery of the cardiovascular system.

22. The system of claim 1, wherein the computed estimates are uncalibrated estimates.

23. A method for predicting or detecting circulatory shock, the method comprising:
   receiving measurements of arterial blood pressure;
   computing mean arterial blood pressure from the received arterial blood pressure measurements;
   computing estimates, based on the received arterial blood pressure measurements, of heart rate, total peripheral resistance, cardiac output, ejection fraction, and ventricular end-diastolic volume; and
   selecting a type of circulatory shock, from a plurality of types of circulatory shock, based on the computed mean arterial blood pressure and the computed estimates.

24. The method of claim 23, further comprising receiving electrocardiograph measurements, wherein selecting a type of circulatory shock is also based on the electrocardiograph measurements.

25. The method of claim 23, further comprising displayed at least one of the received measurements and the computed estimates.

26. The method of claim 23, further comprising displaying the selected type of circulatory shock.

27. The method of claim 23, wherein the type of circulatory shock is determined to be one of septic shock, hypovolemic shock, anaphylactic shock, and cardiogenic shock.

28. The method of claim 23, wherein the computed mean arterial blood pressure and the computed estimates are each classified as one of low, normal and high.

29. The method of claim 28, wherein the type of circulatory shock is determined to be one of septic shock, hypovolemic shock, anaphylactic shock, and cardiogenic shock.

30. The method of claim 29, wherein the type of circulatory shock is determined to be one or more of:

(A) septic shock if the mean arterial blood pressure is low, total peripheral resistance is low, heart rate is high, ejection fraction is normal or high, and cardiac output is low or high;
(B) hypovolemic shock if the mean arterial blood pressure is low, total peripheral resistance is high, heart rate is high, ejection fraction is normal or high, end-diastolic volume is low, and cardiac output is low or high;
(C) anaphylactic shock if the mean arterial blood pressure is low, total peripheral resistance is low, heart rate is high, ejection fraction is normal or high, and cardiac output is high; and
(D) cardiogenic shock if the mean arterial blood pressure is low, total peripheral resistance is high, ejection fraction is low, end-diastolic volume is high, and cardiac output is low.

31. The method of claim 23, 27, 29, or 30, wherein the selecting is done using a lookup table.

32. The method of claim 23, 27, 29, or 30, wherein the selecting is done using population-specific data.

33. The method of claim 23, 27, 29, or 30, wherein the selecting is done using patient-specific data.

34. The method of claim 23, 27, 29, or 30, wherein the selecting is done using a machine learning algorithm.

35. The method of claim 34, wherein the machine learning algorithm includes a Bayesian network.

36. The method of claim 34, wherein the machine learning algorithm includes a neural network.

37. The method of claim 34, wherein the machine learning algorithm includes a fuzzy logic model.

38. The method of claim 23, wherein the arterial blood pressure is central arterial blood pressure.

39. The method of claim 23, wherein the arterial blood pressure is peripheral arterial blood pressure.

40. The method of claim 23, wherein the arterial blood pressure is pulmonary arterial blood pressure.

41. The method of claim 23, wherein the computed estimates are uncalibrated estimates.

* * * * *